(12) United States Patent
Korzinov et al.

(10) Patent No.: US 7,099,715 B2
(45) Date of Patent: Aug. 29, 2006

(54) DISTRIBUTED CARDIAC ACTIVITY MONITORING WITH SELECTIVE FILTERING

(75) Inventors: Lev Korzinov, San Diego, CA (US); Dave Churchville, San Diego, CA (US); Zach Cybulski, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 164 days.

(21) Appl. No.: 10/781,045

(22) Filed: Feb. 17, 2004

(65) Prior Publication Data

US 2005/0182334 A1 Aug. 18, 2005

(51) Int. Cl.
*A61B 5/0432* (2006.01)

(52) U.S. Cl. ...................... 600/509; 128/901

(58) Field of Classification Search ............. 600/509, 600/516, 517, 522, 523; 128/901, 902; 607/30
See application file for complete search history.

(56) References Cited

U.S. PATENT DOCUMENTS

| | | | | |
|---|---|---|---|---|
| 3,593,705 A * | 7/1971 | Thomas et al. | ............. | 600/516 |
| 3,672,353 A * | 6/1972 | Crovella et al. | ............. | 600/515 |
| 4,665,919 A * | 5/1987 | Mensink et al. | ............... | 607/25 |
| 4,887,609 A * | 12/1989 | Cole, Jr. | ..................... | 600/509 |
| 4,938,228 A * | 7/1990 | Righter et al. | ............... | 600/503 |
| 4,989,610 A * | 2/1991 | Patton et al. | ............... | 600/508 |
| 5,217,021 A * | 6/1993 | Steinhaus et al. | ............ | 600/515 |
| 5,255,186 A * | 10/1993 | Steinhaus et al. | ............ | 600/519 |
| 5,273,049 A * | 12/1993 | Steinhaus et al. | ............ | 600/508 |
| 5,437,285 A * | 8/1995 | Verrier et al. | ................ | 600/515 |
| 5,718,242 A * | 2/1998 | McClure et al. | ............. | 600/515 |
| 5,827,195 A * | 10/1998 | Lander | ........................ | 600/509 |
| 5,871,507 A | 2/1999 | Obel et al. | | |
| 5,921,940 A * | 7/1999 | Verrier et al. | ................ | 600/518 |
| 6,115,628 A * | 9/2000 | Stadler et al. | ................ | 600/517 |
| 6,167,258 A * | 12/2000 | Schmidt et al. | ............. | 455/419 |
| 6,668,189 B1 * | 12/2003 | Kaiser et al. | ............... | 600/518 |
| 6,711,438 B1 * | 3/2004 | McClure et al. | ............... | 607/9 |
| 6,834,204 B1 * | 12/2004 | Ostroff et al. | ................. | 607/2 |
| 6,915,156 B1 * | 7/2005 | Christini et al. | ............. | 600/509 |

OTHER PUBLICATIONS

Burdick Quest® Exercise Stress System http://web.archive.org/web/20030412172127/www.burdick.com/exercisestress.html ☐Available on or before Apr. 12, 2003.*

* cited by examiner

*Primary Examiner*—Robert Pezzuto
*Assistant Examiner*—Yun Haeng Lee
(74) *Attorney, Agent, or Firm*—Fish & Richardson P.C.

(57) ABSTRACT

System and techniques for distributed monitoring of cardiac activity include selective T wave filtering. In general, in one implementation, a distributed cardiac activity monitoring system includes a monitoring apparatus, with a selectively activated T wave filter, and a monitoring station. The monitoring apparatus can include a communications interface, a real-time QRS detector, a T wave filter, and a selector that activates the T wave filter to preprocess a cardiac signal provided to the real-time QRS detector in response to a message. The monitoring station can communicatively couple with the monitoring apparatus, over a communications channel, via the communications interface and can transmit the message to the monitoring apparatus to activate the T wave filter based at least in part upon a predetermined criteria (e.g., abnormal T waves for an individual, as identified by a system operator).

34 Claims, 4 Drawing Sheets

DISTRIBUTED CARDIAC ACTIVITY MONITORING WITH SELECTIVE FILTERING

BACKGROUND

The present application describes systems and techniques relating to monitoring cardiac activity, for example, processing cardiac electrical activity to determine heart rate.

The electrical activity of the heart can be monitored to track various aspects of the functioning of the heart. Given the volume conductivity of the body, electrodes on the body surface or beneath the skin can display potential differences related to this activity. Anomalous electrical activity can be indicative of disease states or other physiological conditions ranging from benign to fatal.

Cardiac monitoring devices can sense the cardiac electrical activity of a living being and identify heart beats. Frequently, identification of heart beats is performed by identifying the R waves in the QRS complex, as can be seen in an electrocardiogram (ECG). The R wave is the first positive deflection in the QRS complex, representing ventricular depolarization. The typically large amplitude of this positive deflection in the QRS complex is useful in identifying a heart beat.

SUMMARY

In general, in one aspect, a distributed cardiac activity monitoring system includes a monitoring apparatus, with a selectively activated T wave filter, and a monitoring station. The monitoring apparatus can include a communications interface, a real-time QRS detector, a T wave filter, and a message-activated selector that activates the T wave filter with respect to the real-time QRS detector to preprocess a cardiac signal provided to the real-time QRS detector. The monitoring station can communicatively couple with the monitoring apparatus, over a communications channel, via the communications interface and can transmit the message to the monitoring apparatus to activate the T wave filter based at least in part upon a predetermined criteria (e.g., abnormal T waves for an individual, as identified by a system operator).

The details of one or more embodiments are set forth in the accompanying drawings and the description below. Other features and advantages will become apparent from the description, the drawings, and the claims.

DETAILED DESCRIPTION

Figure 1:
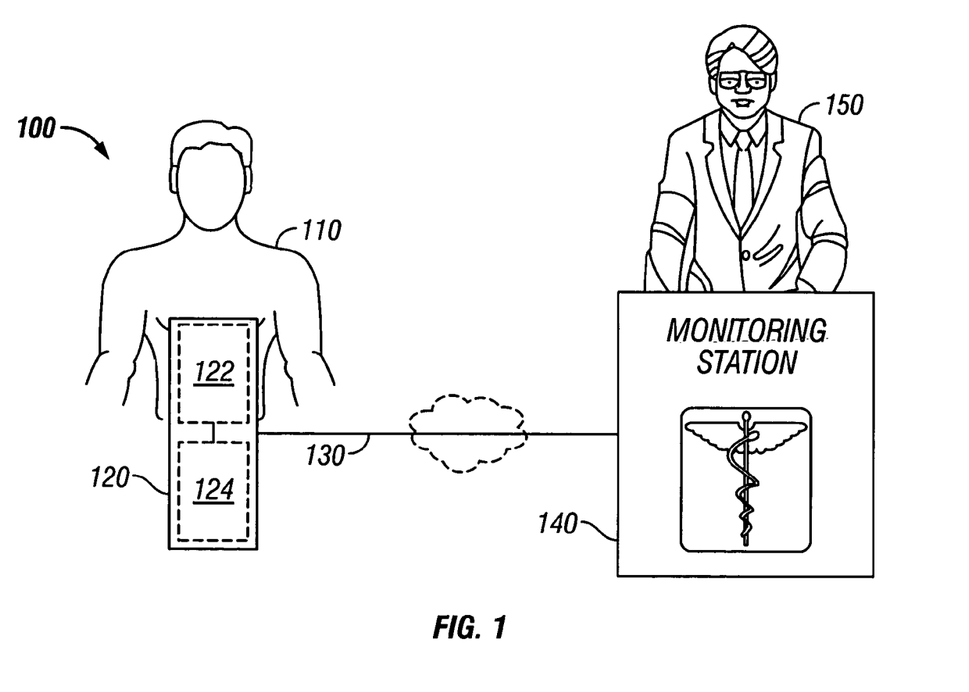
FIG. 1 illustrates a distributed cardiac activity monitoring system in which a cardiac signal is monitored for medical purposes.

FIG. 1 illustrates a distributed cardiac activity monitoring system 100 in which a cardiac signal is monitored for medical purposes. A living being 110 (e.g., a human patient, including potentially a healthy patient for whom cardiac monitoring is nonetheless deemed appropriate) has a cardiac monitoring apparatus 120 configured to obtain cardiac signals from the patient's heart. The cardiac monitoring apparatus 120 can be composed of one or more devices, such as a sensing device 122 and a processing device 124. The cardiac monitoring apparatus 120 can communicate with a monitoring station 140 (e.g., a computer in a monitoring center) via a communications channel 130. The cardiac monitoring apparatus 120 can include one or more sensing, calibration, signal processing, control, data storage, and transmission elements suitable for generating and processing the cardiac signal, as well as for relaying all or a portion of the cardiac signal over the communications channel 130. The communications channel 130 can be part of a communications network and can include any suitable medium for data transmission, including wired and wireless media suitable for carrying optical and/or electrical signals.

The cardiac monitoring apparatus 120 can communicate sensed cardiac signals (e.g, ECG data), cardiac event information (e.g., real-time heart rate data), and additional physiological and/or other information to the monitoring station 140. The cardiac monitoring apparatus 120 can include an implantable medical device, such as an implantable cardiac defibrillator and an associated transceiver or pacemaker and an associated transceiver, or an external monitoring device that the patient wears. Moreover, the cardiac monitoring apparatus 120 can be implemented using, for example, the CardioNet Mobile Cardiac Outpatient Telemetry (MCOT) device, which is commercially available and provided by CardioNet, Inc of San Diego, Calif.

The monitoring station 140 can include a receiver element for receiving transmitted signals, as well as various data processing and storage elements for extracting and storing information carried by transmissions regarding the state of the individual 110. The monitoring station 140 can be located in the same general location (e.g., in the same room, building or health care facility) as the monitoring apparatus 120, or at a remote location. The monitoring station 140 can include a display and a processing system, and a system operator 150 (e.g., a doctor or a cardiovascular technician) can use the monitoring station 140 to evaluate physiological data received from the cardiac monitoring apparatus 120. The system operator 150 can use the monitoring station 140 to change operational settings of the cardiac monitoring apparatus 120 remotely during active cardiac monitoring of the living being 110. Moreover, the cardiac monitoring apparatus 120 can selectively activate a T wave filter in response to discovery of a predetermined characteristic in the sensed cardiac signal, such as described further below. For example, the system operator can determine that the patient has consistently abnormal T waves and cause the monitoring station 140 to send a message to the monitoring apparatus 120 to activate the T wave filter.

Figure 2:
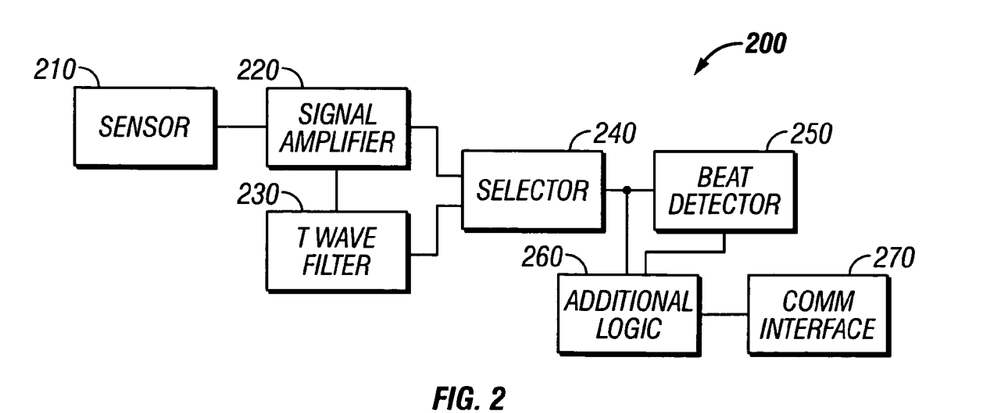
FIG. 2 illustrates an example cardiac monitoring apparatus used with a living being.

FIG. 2 illustrates an example cardiac monitoring apparatus 200 used with a living being. The apparatus 200 can include a sensor 210, a signal amplifier 220, a T wave filter 230, a selector 240, a beat detector 250, additional logic 260, and a communications interface 270. The sensor 210 can include two or more electrodes subject to one or more potential differences that yield a voltage signal, such as the signals illustrated in FIGS. 3 and 4. The electrodes can be body surface electrodes such as silver/silver chloride electrodes and can be positioned at defined locations to aid in monitoring the electrical activity of the heart. The sensor 210 can also include leads or other conductors that form a signal path to the signal amplifier 220. The signal amplifier 220 can receive and amplify the voltage signals.

Furthermore, the signal amplifier 220 can include additional processing logic. For example, the additional processing logic can perform filtering and analog-to-digital conversion; the T wave filter 230 can be integrated into the signal amplifier 220. Additional processing logic can also be implemented elsewhere in the apparatus 200, and the amplification and other additional processing can occur before or after digitization. The signal amplifier 220 can provide an amplified and processed signal to the T wave filter 230 and to the selector 240. Moreover, some of the additional processing logic discussed in connection with FIG. 2 can also be implemented in the monitoring station 140.

The various components of the apparatus 200 can be implemented as analog or digital components. For example, the selector 240 can be analog, selective activation circuitry that selects one of its two inputs (from the signal amplifier 220 and from the T wave filter 230) to be provided to the beat detector 250. Alternatively, the selector 240 can enable and disable the T wave filter 230 (e.g., the T wave filter 230 can be integrated into the beat detector 250 and turned on and off as needed). In general, the selector 240 activates the T wave filter 230 with respect to the heart beat detector 250, to preprocess the signal, in response to a message (e.g., a message received from the monitoring station 140 or a message generated within the apparatus 200).

The beat detector 250 is a component (e.g., analog circuitry or digital logic) that identifies the time period between ventricular contractions. For example, the beat detector 250 can be a real-time QRS detector that identifies successive QRS complexes, or R waves, and determines the beat-to-beat timing in real time (i.e., output data is generated directly from live input data). The beat-to-beat timing can be determined by measuring times between successive R-waves. The beat detector 250 can provide information regarding the time period between ventricular contractions to additional logic 260. The additional logic 260 can include logic to determine if an abnormal T wave potentially is occurring based on signal morphology analysis, an atrial fibrillation/atrial flutter (AF) detector, AF decision logic, and an event generator. The heart rate information can be transmitted using the communications interface 270, which can be a wired or wireless interface. Moreover, the sensed cardiac signal, or portions thereof, can be sent to a monitoring station, periodically, upon being interrogated and/or in response to identified events/conditions.

The morphology of a cardiac signal can vary significantly from patient to patient. Sometimes, the patient's ECG has a very tall T wave, which might result in false classification of this T wave as an R wave. When this happens, the heart rate reported by the apparatus may be twice the real heart rate, and the morphology of beats may not be detected correctly. The T wave filter 230 can reduce the amplitude of T waves, while preserving or slightly increasing the amplitude of R waves.

Figure 3:
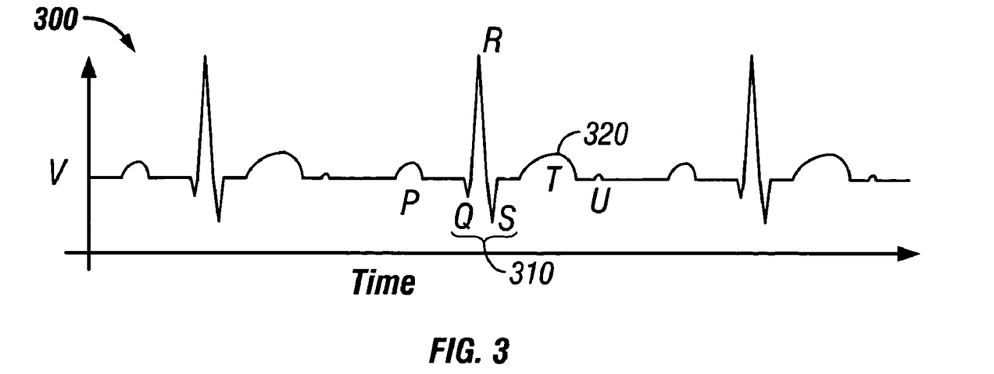
FIG. 3 illustrates an example ECG of a normal patient.
Figure 4:
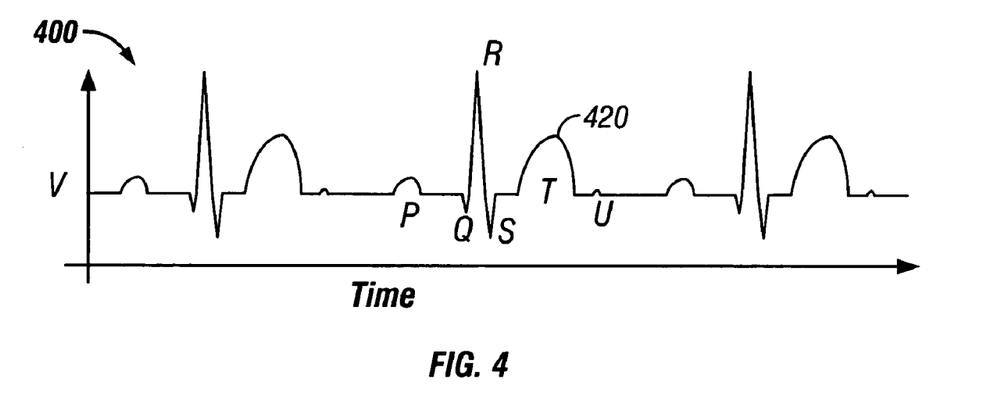
FIG. 4 illustrates an example ECG of a patient with abnormal T waves.

FIG. 3 illustrates an example ECG 300 of a normal patient. The heart cycle has four generally recognized waveforms: the P wave, the QRS complex, the T wave, and the U wave. The relative sizes of a QRS complex 310 and a T wave 320 represent the signal from a typical heart. FIG. 4 illustrates an example ECG 400 of a patient with abnormal T waves. As shown, a T wave 420 is tall in comparison with a normal T wave 320, and the rest of the cardiac cycle looks the same. In general, abnormal T waves can result in misclassification of T waves as R waves. In these cases, the T wave filter can be selectively applied to improve cardiac monitoring performance. The reduction in amplitude of the T wave may be up to 80% (five times) and can thus create a significant increase in the accuracy of QRS detection in patients with abnormal T waves.

Figure 5:
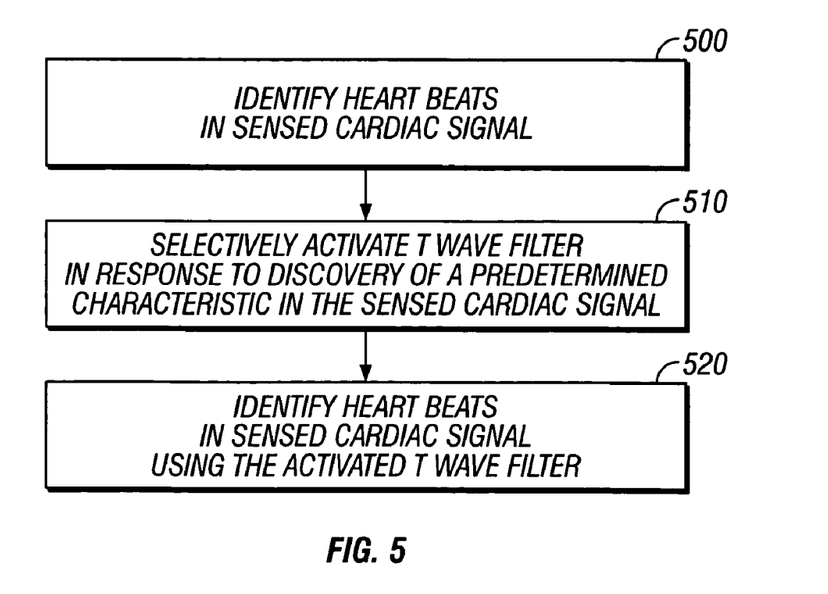
FIG. 5 illustrates a process of selectively activating a T wave filter.

FIG. 5 illustrates a process of selectively activating a T wave filter. Heart beats are identified in sensed cardiac signals at 500. A T wave filter is selectively activated in response to discovery of a predetermined characteristic in the sensed cardiac signal at 510. The discovery of the predetermined characteristic can involve an operator's identification of a tall T wave in at least a portion of the sensed cardiac signal, and activating the T wave filter can improve the cardiac monitoring. After filter activation, heart beats are identified in sensed cardiac signals using the activated T wave filter at 520. The T wave filter can be a custom highpass-like filter. The filter can be such that it reduces signal amplitude at low frequencies of the sensed cardiac signal and increases signal amplitude at high frequencies of the sensed cardiac signal.

Figure 6:
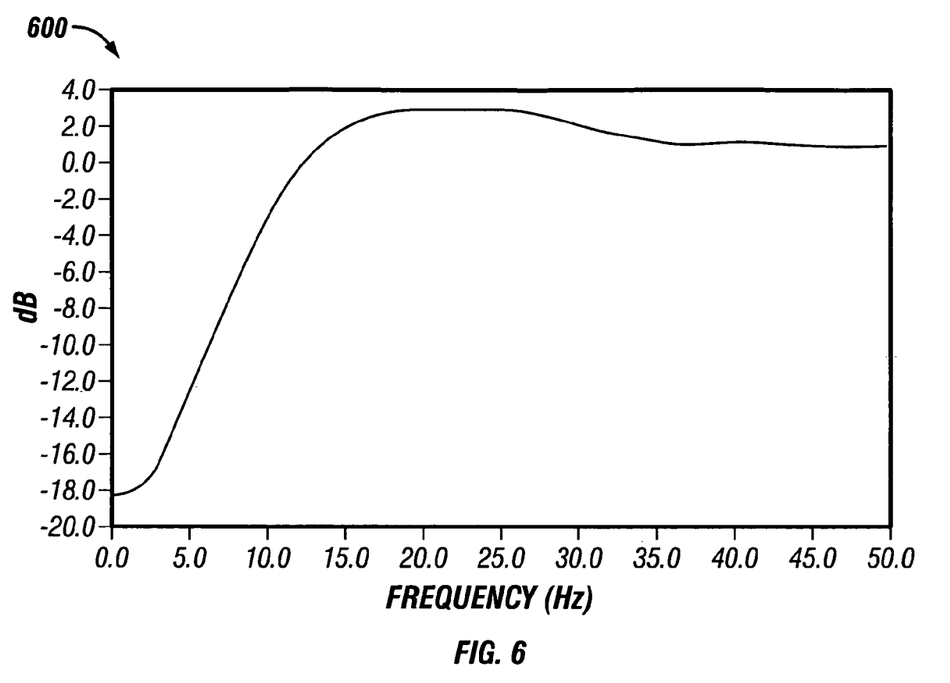
FIG. 6 illustrates a frequency response of an example T wave filter.
Figure 7:
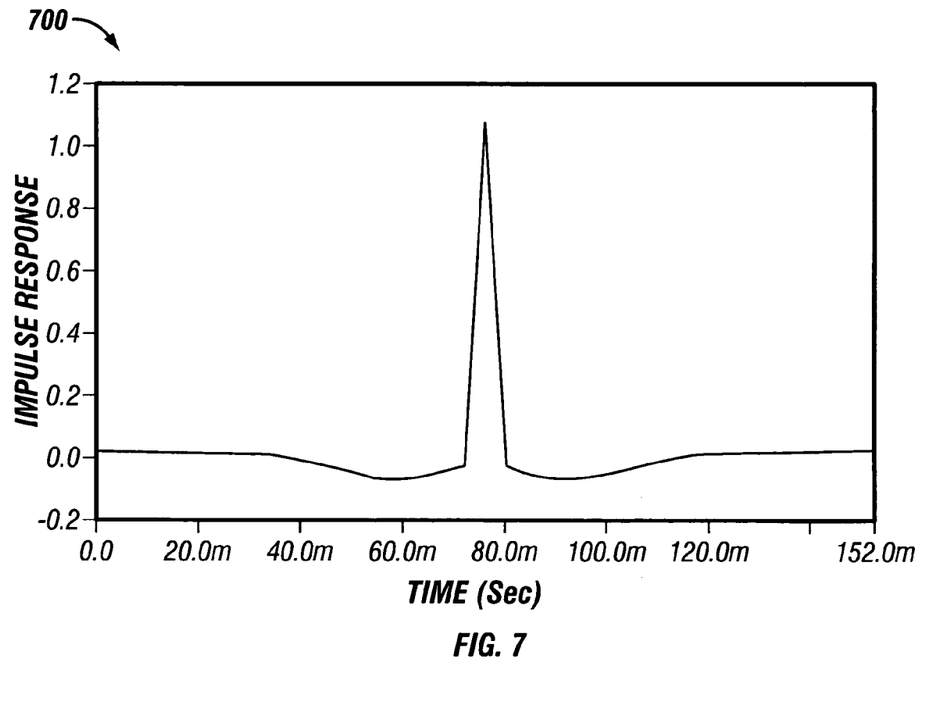
FIG. 7 illustrates an impulse response of an example T wave filter.

FIG. 6 illustrates a frequency response 600 of an example T wave filter. As shown, the filter's frequency response can be less than or equal to −10 dB in the low frequency range of 0–5 Hertz (Hz). This frequency range is where T wave power spectrum is predominantly located. At higher frequencies, the filter can preserve and/or increase the amplitude of the signal (e.g., modify the signal by 0 dB or more for frequencies above 10 Hz), which can increase the amplitude of the R wave and make the beat detection more reliable. As shown, the filter's frequency response can be +2 dB or more in a high frequency range of 20–25 Hz. FIG. 7 illustrates an impulse response 700 of the example T wave filter illustrated in FIG. 6.

Figure 8:
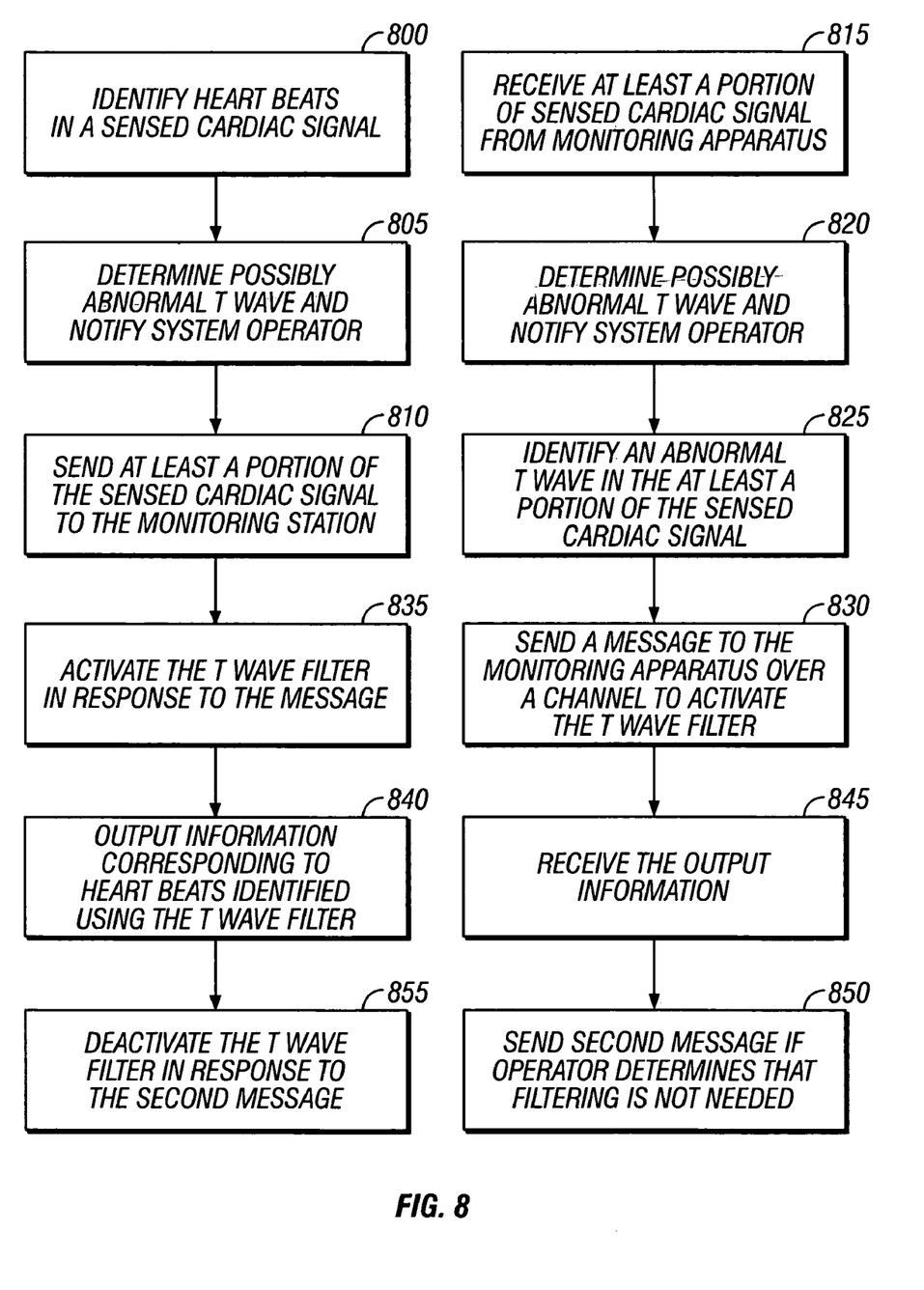
FIG. 8 illustrates an example distributed process for selectively activating a T wave filter.

FIG. 8 illustrates an example distributed process for selectively activating a T wave filter. Heart beats are identified in a sensed cardiac signal at 800. The cardiac signal can be from a monitoring apparatus in contact with a living being under active cardiac monitoring, as described above. A possibly abnormal T wave can be determined in a post-processing operation that analyzes signal morphology, and a system operator can be notified of the possible abnormal T wave at 805; this operation can alternatively be done at the monitoring station, as mentioned below. This can assist the operator in identifying patients that may benefit from having the T wave filter activated in their monitors. Additionally, the operator can proactively check the sensed cardiac signal from the monitor to assess the T waves.

At least a portion of the sensed cardiac signal can be sent to a monitoring station at 810. This can involve continuously or periodically sending the cardiac signal, or sending the cardiac signal in response to identified events/conditions, such as the identification of the possible abnormal T wave at 805. The sensed cardiac signals are received from the monitoring apparatus at 815. A possibly abnormal T wave can be determined using a signal morphology analyzer, and a system operator can be notified of the possible abnormal T wave at 820.

An abnormal T wave can be identified, such as by a system operator, in the received cardiac signal at 825, and a message can be sent to the monitoring apparatus over a communications channel at 830. The message causes the monitoring apparatus to activate a T wave filter used in identifying heart beats of the living being under active cardiac monitoring. The T wave filter is activated in response to the message at 835. Information corresponding to the heart beats identified using the T wave filter (e.g., heart rate data) can be output to the communications channel at 840. This information can be received at the monitoring station at 845.

Moreover, if the system operator subsequently determines that the T wave filter is not needed for the patient, a message to deactivate the T wave filter can be sent at 850, and the T wave filter can be deactivated in response to this second message at 855. The T wave filter may not distinguish morphology of the beat. Therefore, slow ventricular beats, such as premature ventricular contractions (PVCs), or some ectopic beats may also be reduced in amplitude when the filter is applied. In cases where multiple PVCs are monitored, the T wave filter may reduce the amplitude of these beats, and thus a pause or asystole event may be generated, which generally should alert the system operator to deactivate the T wave filter. However, this may not be relevant in the particular application as many cardiac monitoring applications do not require monitoring of PVCs or ectopic beats.

Fast ventricular beats (with a rate over 100 beats per minute) may be left unchanged by the T wave filter because their power spectrum is usually above 10 Hz. The T wave filter described can be installed into a monitoring apparatus that includes a preexisting beat detector. The T wave filter can preprocess the input provided to the preexisting beat detector, improving the functioning of the beat detector for individuals with abnormal T waves, even though the preexisting beat detector was designed without a T wave filter in mind. The T wave filter can be in a disabled state by default and may be turned on only for the monitors used with those individuals with abnormal T waves (e.g., patients whose cardiac signal features constant tall T waves).

The systems and techniques described and illustrated in this specification can be implemented in analog electronic circuitry, digital electronic circuitry, integrated circuitry, computer hardware, firmware, software, or in combinations of the forgoing, such as the structural means disclosed in this specification and structural equivalents thereof. Apparatus can be implemented in a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) optical disks, such as CD-ROM disks. Any of the foregoing can be supplemented by, or incorporated in, ASICs (application-specific integrated circuits).

To provide for interaction with a user (such as the system operator), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users and operational settings can be changed in the monitoring system.

Finally, while the foregoing system has been described in terms of particular implementations, other embodiments are within the scope of the following claims.

What is claimed is:

1. A machine-implemented method comprising:
   identifying heart beats in a sensed cardiac signal;
   activating a T wave filter frequency domain, used in said identifying heart beats, in response to a message from a monitoring station generated at least in part based upon discovery of a predetermined characteristic in the sensed cardiac signal; and
   outputting information corresponding to the identified heart beats to a communications channel of a distributed cardiac activity monitoring system.

2. The method of claim 1, wherein said identifying heart beats comprises identifying R waves in the sensed cardiac signal.

3. The method of claim 1, further comprising sending at least a portion of the sensed cardiac signal to the monitoring station, and wherein the discovery of the predetermined characteristic comprises identification of a tall T wave in the at least a portion of the sensed cardiac signal by an operator at the monitoring station.

4. The method of claim 1, wherein said activating the T wave filter frequency domain comprises activating a filter that reduces signal amplitude at low frequencies of the sensed cardiac signal.

5. The method of claim 4, wherein the filter has a frequency response of about 0 dB or more at frequencies above ten Hertz.

6. The method of claim 5, wherein the filter has a frequency response of about −10 dB or less in a low frequency range of zero to five Hertz.

7. The method of claim 6, wherein the filter has a frequency response of about +2 dB or more in a high frequency range of twenty to twenty five Hertz.

8. The method of claim 1, wherein said outputting information comprises outputting heart rate data to a wireless communications channel.

9. The method of claim 1, further comprising:
   determining that an abnormal T wave is possible based on signal morphology analysis; and
   notifying a system operator of the possible abnormal T wave.

10. The method of claim 1, further comprising deactivating the T wave filter frequency domain in response to a second message.

11. A distributed cardiac activity monitoring system comprising:
- a monitoring apparatus including a communications interface, a real-time QRS detector, a T wave filter frequency domain, and a selector that activates the T wave filter with respect to the real-time QRS detector in response to a message, wherein the activated T wave filter frequency domain preprocesses a cardiac signal provided to the real-time QRS detector; and
- a monitoring station that communicatively couples with the monitoring apparatus via the communications interface and transmits the message to the monitoring apparatus to activate the T wave filter frequency domain based at least in part upon a predetermined criteria.

12. The system of claim 11, wherein the communications interface comprises a wireless communications interface.

13. The system of claim 11, wherein the T wave filter frequency domain comprises a filter that reduces signal amplitude at low frequencies.

14. The system of claim 13, wherein the filter has a frequency response of about −10 dB or less in a low frequency range of zero to five Hertz.

15. The system of claim 13, wherein the filter has a frequency response of about 0 dB or more at frequencies above ten Hertz.

16. The system of claim 15, wherein the filter has a frequency response of about +2 dB or more in a high frequency range of twenty to twenty five Hertz.

17. The system of claim 11, wherein the selector comprises analog, selective activation circuitry.

18. The system of claim 11, wherein the monitoring apparatus further comprises additional logic that determines if an abnormal T wave is possible based on signal morphology analysis, and notifies a system operator of the possible abnormal T wave.

19. The system of claim 11, wherein the monitoring station further comprises additional logic that determines if an abnormal T wave is possible based on signal morphology analysis, and notifies a system operator of the possible abnormal T wave.

20. A cardiac monitoring apparatus comprising:
- a communications interface;
- a real-time heart beat detector;
- a T wave filter frequency domain; and
- a selector that activates the T wave filter frequency domain with respect to the real-time heart beat detector in response to a message, wherein the activated T wave filter frequency domain preprocesses a cardiac signal provided to the real-time heart beat detector.

21. The apparatus of claim 20, wherein the communications interface comprises a wireless communications interface.

22. The apparatus of claim 20, wherein the real-time heart beat detector comprises an analog heart beat detector, the T wave filter frequency domain comprises an analog T wave filter, and the selector comprises analog, selective activation circuitry.

23. The apparatus of claim 20, wherein the T wave filter frequency domain comprises a filter that reduces signal amplitude at low frequencies.

24. The apparatus of claim 23, wherein the filter has a frequency response of about −10 dB or less in a low frequency range of zero to five Hertz.

25. The apparatus of claim 24, wherein the filter has a frequency response of about 0 dB or more at frequencies above ten Hertz.

26. The apparatus of claim 25, wherein the filter has a frequency response of about +2 dB or more in a high frequency range of twenty to twenty five Hertz.

27. The apparatus of claim 20, further comprising additional logic that determines if an abnormal T wave is possible based on signal morphology analysis, and notifies a system operator of the possible abnormal T wave.

28. A method comprising:
- receiving at least a portion of a sensed cardiac signal from a monitoring apparatus in contact with a living being under active cardiac monitoring;
- identify an abnormal T wave in the received cardiac signal; and
- sending a message to the monitoring apparatus over a communications channel, the message causing the monitoring apparatus to activate a T wave filter frequency domain used in identifying heart beats of the living being under active cardiac monitoring.

29. The method of claim 28, further comprising:
- determining that an abnormal T wave is possible based on signal morphology analysis; and
- notifying a system operator of the possible abnormal T wave, wherein the system operator performs said identifying the abnormal T wave.

30. The method of claim 28, wherein said sending the message comprises sending the message over a wireless communications channel.

31. The method of claim 28, further comprising installing the T wave filter frequency domain into the monitoring apparatus, which comprises a preexisting beat detector.

32. A system comprising:
- means for identifying heart beats in a sensed cardiac signal;
- means for filtering the sensed cardiac signal to reduce T waves in the sensed cardiac signal; and
- means for selectively activating the means for filtering in response to discovery of a predetermined characteristic in the sensed cardiac signal.

33. The system of claim 32, further comprising means for alerting a system operator of a possible abnormal T wave.

34. The system of claim 32, wherein the means for filtering comprises means for generally highpass filtering.

* * * * *

UNITED STATES PATENT AND TRADEMARK OFFICE
CERTIFICATE OF CORRECTION

PATENT NO. : 7,099,715 B2
APPLICATION NO. : 10/781045
DATED : August 29, 2006
INVENTOR(S) : Lev Korzinov, Dave Churchville and Zach Cybulski It is certified that error appears in the above-identified patent and that said Letters Patent is hereby corrected as shown below:

In Claim 1, col. 6 line 29, replace "T wave filter frequency domain" with --frequency domain T wave filter--;

In Claim 4, col. 6 line 46, replace "T wave filter frequency domain" with --frequency domain T wave filter--;

In Claim 10, col. 7 line 2, replace "T wave filter frequency domain" with --frequency domain T wave filter--;

In Claim 11, col. 7 lines 4-5, replace "T wave filter frequency domain" with --frequency domain T wave filter--;

In Claim 11, col. 7 lines 7-8, replace "T wave filter frequency domain" with --frequency domain T wave filter--;

In Claim 11, col. 7 line 16, replace "T wave filter frequency domain" with --frequency domain T wave filter--;

In Claim 13, col. 7 line 21, replace "T wave filter frequency domain" with --frequency domain T wave filter--;

In Claim 20, col. 7 line 48, replace "T wave filter frequency domain" with --frequency domain T wave filter--;

In Claim 20, col. 7 line 49, replace "T wave filter frequency domain" with --frequency domain T wave filter--;

In Claim 20, col. 7 line 51, replace "T wave filter frequency domain" with --frequency domain T wave filter--;

UNITED STATES PATENT AND TRADEMARK OFFICE
CERTIFICATE OF CORRECTION

PATENT NO. : 7,099,715 B2
APPLICATION NO. : 10/781045
DATED : August 29, 2006
INVENTOR(S) : Lev Korzinov, Dave Churchville and Zach Cybulski It is certified that error appears in the above-identified patent and that said Letters Patent is hereby corrected as shown below:

In Claim 22, col. 7 lines 56-1, replace "T wave filter frequency domain" with --frequency domain T wave filter--;

In Claim 23, col. 8 line 4, replace "T wave filter frequency domain" with --frequency domain T wave filter--;

In Claim 28, col. 8 line 24, replace "T wave filter frequency domain" with --frequency domain T wave filter--;

In Claim 31, col. 8 line 42, replace "T wave filter frequency domain" with --frequency domain T wave filter--.

Signed and Sealed this

Fifth Day of February, 2008

JON W. DUDAS
*Director of the United States Patent and Trademark Office*